(12) United States Patent
Bedoukian

(10) Patent No.: US 10,077,414 B2
(45) Date of Patent: Sep. 18, 2018

(54) FRAGRANCE COMPOSITIONS CONTAINING ISOMERIC ALKOXYNONENOLS

(71) Applicant: BEDOUKIAN RESEARCH, INC., Danbury, CT (US)

(72) Inventor: Robert H. Bedoukian, West Redding, CT (US)

(73) Assignee: Bedoukian Research, Inc., Danbury, CT (US)

( * ) Notice: Subject to any disclaimer, the term of this patent is extended or adjusted under 35 U.S.C. 154(b) by 0 days.

(21) Appl. No.: 15/657,795

(22) Filed: Jul. 24, 2017

(65) Prior Publication Data

US 2018/0030374 A1    Feb. 1, 2018

Related U.S. Application Data

(60) Provisional application No. 62/368,783, filed on Jul. 29, 2016.

(51) Int. Cl.
| | | |
|---|---|---|
| *C11D 3/50* | (2006.01) | |
| *C11B 9/00* | (2006.01) | |
| *C11C 5/00* | (2006.01) | |
| *A61L 9/01* | (2006.01) | |
| *A61K 8/34* | (2006.01) | |
| *A61Q 5/00* | (2006.01) | |
| *A61Q 15/00* | (2006.01) | |
| *A61Q 9/00* | (2006.01) | |
| *A61Q 19/00* | (2006.01) | |

(52) U.S. Cl.
CPC ............ *C11B 9/0015* (2013.01); *A61K 8/342* (2013.01); *A61L 9/01* (2013.01); *A61Q 5/00* (2013.01); *A61Q 9/00* (2013.01); *A61Q 15/00* (2013.01); *A61Q 19/002* (2013.01); *C11C 5/002* (2013.01); *C11D 3/50* (2013.01)

(58) Field of Classification Search
CPC ...... A61K 8/324; A61K 8/345; C11B 9/0015; C11D 3/50
See application file for complete search history.

(56) References Cited

U.S. PATENT DOCUMENTS

| | | | |
|---|---|---|---|
| 3,028,431 A | 4/1962 | Webb | |
| 3,963,648 A | 6/1976 | Jones et al. | |
| 7,842,842 B1 | 11/2010 | Majeed et al. | |
| 2015/0307439 A1* | 10/2015 | Beumer | A61Q 13/00 426/534 |

FOREIGN PATENT DOCUMENTS

| | | |
|---|---|---|
| CN | 103396296 A | 11/2013 |
| DE | 1232563 B | 1/1967 |
| JP | 2000-319684 | * 11/2000 |

* cited by examiner

*Primary Examiner* — John R Hardee
(74) *Attorney, Agent, or Firm* — Ohlandt, Greeley, Ruggiero & Perle, L.L.P.

(57) ABSTRACT

A composition containing at least one isomeric alkoxynonenol, in particular, isomeric 8-alkoxy-4,8-dimethylnon-1-en-3-ol, in an amount effective to impart a fragrance to the composition. A fragrance composition containing at least one isomeric alkoxynonenol in an amount effective to impart a fragrance to the composition. A consumer product containing the fragrance composition having at least one isomeric alkoxynonenol in an amount effective to impart a fragrance to the composition. A method of imparting a fragrance to a consumer product by adding to the consumer product a fragrance composition containing at least one isomeric alkoxynonenol in an amount effective to impart a fragrance to the consumer product.

20 Claims, No Drawings

FRAGRANCE COMPOSITIONS CONTAINING ISOMERIC ALKOXYNONENOLS

RELATED APPLICATION

This application claims the benefit of copending U.S. Application No. 62/368,783, filed Jul. 29, 2016, which is incorporated herein by reference in its entirety.

BACKGROUND OF THE DISCLOSURE

1. Field of the Disclosure

This disclosure relates to fragrance compositions containing isomeric alkoxynonenols, in particular, isomeric 8-alkoxy-4,8-dimethylnon-1-en-3-ols. This disclosure also relates to a method of imparting a fragrance to a consumer product by adding fragrance compositions containing isomeric alkoxynonenols to the consumer product.

2. Description of the Related Art

Various alkoxyalcohols are known as fragrance materials. For example, U.S. Pat. No. 3,963,648 describes specifically 7-alkoxy-3,7-dimethyloctan-2-ol as possessing an attractive sandalwood odor.

Chinese Patent No. 103396296 B describes a series of 2,6-dimethyl-6-methoxy-heptanol derivatives with basically fruity, marine odor.

German Auslegeschrift No. 1232563 describes a process for producing citronellol derivatives by reducing 3,7-dimethyloctan-1,2-epoxides which are substituted in the 7 position by a hydroxy, alkoxy or acyloxy group. The process inevitably produces mixtures of citronellol and elgenol derivatives. In particular, the reduction of 7-methoxy-3,7-dimethyloctan-1,2-epoxide is described which produces a mixture of methoxy citronellol and methoxy elgenol. The latter is described as an unwanted by product whose isolation is not described. Elgenol (2, 6 dimethyl octan 2-ol) and methoxycitronellol (7-methoxy-3,7-dimethyloctanol) exhibit no trace of any sandalwood odor.

There is an ongoing interest in the fragrance industry to use new compounds that enhance or improve organoleptic character and impart new notes to help perfumers create exciting new fragrance experience desired by consumers. There remains a need and demand for unique fragrance compositions.

The present disclosure provides many advantages, including access to novel and exciting notes, which shall become apparent as described below.

SUMMARY OF THE DISCLOSURE

This disclosure relates in part to fragrance compositions containing isomeric alkoxynonenols, in particular, isomeric 8-alkoxy-4,8-dimethylnon-1-en-3-ols.

This disclosure also relates in part to a composition comprising at least one isomeric alkoxynonenol, in particular, isomeric 8-alkoxy-4,8-dimethylnon-1-en-3-ol, in an amount effective to impart a fragrance to the composition.

This disclosure further relates in part to a consumer product containing the fragrance composition comprising at least one isomeric alkoxynonenol, in particular, isomeric 8-alkoxy-4,8-dimethylnon-1-en-3-ol, in an amount effective to impart a fragrance to the consumer product.

This disclosure yet further relates in part to a method of imparting a fragrance to a consumer product by adding fragrance compositions containing isomeric alkoxynonenols, in particular, isomeric 8-alkoxy-4,8-dimethylnon-1-en-3-ols, to the consumer product.

Further, in accordance with this disclosure, it has been surprisingly found that isomeric alkoxynonenols, in particular, isomeric 8-alkoxy-4,8-dimethylnon-1-en-3-ols, impart milky and creamy sandalwood odor with shades of floral notes to perfume formulations.

Further objects, features and advantages of the present disclosure will be understood by reference to the following detailed description.

DESCRIPTION OF THE PREFERRED EMBODIMENTS

In accordance with this disclosure, isomeric alkoxynonenols, in particular, isomeric 8-alkoxy-4,8-dimethylnon-1-en-3-ols, have been found to be useful in the field of perfumery as perfuming ingredients. It has been discovered that isomeric alkoxynonenols, in particular, isomeric 8-alkoxy-4,8-dimethylnon-1-en-3-ols, have a marked sandalwood odor with floral undertones, particularly of rose. These creamy and strong sandalwood/floral middle notes can uniquely bridge the heavy woody base notes usually associated with the majority of other sandalwood materials derived from campholene aldehyde (e.g., polysantol, Javanol, etc.) or isobornylcyclohexanol (sandela/sandiff) moieties and lift them to be perceived throughout the composition including the top notes. Furthermore, it is indeed surprising to find the isomeric alkoxynonenols, in particular, isomeric 8-alkoxy-4,8-dimethylnon-1-en-3-ols, of this disclosure having such a distinct sandalwood odor, since the related aliphatic alkanols generally have odors that can best be described as citrus and floral rather than sandalwood.

As used herein, the term "perfume composition" refers a mixture of fragrance materials and optionally auxiliary substances, dissolved in a suitable solvent or mixed with a powdery substrate which is used to impart a desired odor to the skin and/or all types of products. Examples of such products include soaps, detergents, air fresheners, room sprays, pomanders, candles, cosmetics, such as creams, ointments, toilet waters, pre- and aftershave lotions, talcum powders, hair-care agents, body deodorants and anti-perspirants.

As used herein, the term "fragrance composition" refers to a mixture comprising one or more fragrance components, in any of their forms, and one or more solvents or perfuming co-ingredients. As known in the art, a fragrance composition will contain one or more fragrance components (e.g., perfuming co-ingredients) in order to impart an olfactory note to the composition (e.g., a household cleaner, perfume, or other commercial product) to which it is added. In one embodiment, the fragrance composition contains two or more fragrance components which, collectively and in combination with the solvent to which they are added, impart an intended olfactory note (e.g., a hedonically pleasing note) to a human in close proximity to the fragrance composition.

In general terms, perfuming co-ingredients belong to chemical classes as varied as alcohols, aldehydes, ketones, esters, ethers, acetates, nitriles, terpene hydrocarbons, nitrogenous or sulphurous heterocyclic compounds and essential oils of natural or synthetic origin, and are known to perfumists of ordinary skill in the art. Many of these ingredients are listed in reference texts such as S. Arctander, Perfume and Flavor Chemicals, 1969, Montclair, N.J., USA or any of its more recent versions, each of which are hereby incorporated by reference.

Fragrance materials and mixtures of fragrance materials which can be used in combination with the compounds according to this disclosure for manufacturing perfume compositions are, for example, natural products, such as essential oils, absolutes, resinoids, resins, concretes, etc., but also synthetic fragrance materials such as hydrocarbons, alcohols, aldehydes, ketones, ethers, acids, esters, acetals, ketals, nitriles, etc., including saturated and unsaturated compounds, aliphatic carbocyclic and heterocyclic compounds.

Examples of fragrance materials which can be used in combination with the compounds according to the disclosure include geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethyl-benzyl carbinol, trichloromethylphenyl carbinyl acetate, p-tert-butylcyclohexyl acetate, isononyl acetate, vetiveryl acetate, vetiverol, alpha-hexyl-cinnam-aldehyde, 2-methyl-3-(p-tert-butylphenyl)-propanal, 2-methyl-3-(p-isopropylphenyl)-propanal, 3-(p-tert-butylphenyl)-propanal, tricyclodecenyl acetate, tricyclodecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy-3-pentyl-tetrahydropyran, 3-carboxymethyl-2-pentylcyclopentane, 2-n-heptylcyclopentanone, 3-methyl-2-pentyl-2-cyclopentenone, n-decanal, n-dodecanal, 9-decen-1-ol, phenoxyethylisobutyrate, phenylacetaldehydedi-methylacetal, phenylacetaldehyde-diethylacetal, geranylnitrile, citronellylnitrile, cedrylacetate, 3-isocamphylcyclohexanol, cedrylmethyl ether, isolongifolanone, aubepinitrile, aubepine, heliotripine, coumarin, eugenol, vanillin, diphenyl oxide, hydroxycitronellal, ionones, methylionones, isomethylionones, irones, cis-3-hexenol and esters of the latter, indan-musks, tetraline-musks, isochromane-musks, macrocyclic ketones, macrolactone-musks, ethylene brassylate, aromatic nitromusks, and the like to mention a few.

Auxiliary substances and solvents which can be used in perfume compositions which contain compounds according to this disclosure include, for example: ethanol, isopropanol, dipropylene glycol, dipropyleneglycol monomethyl ether, diethylphthalate, and the like.

The perfumery compositions of this disclosure may be compounded according to recognized techniques of perfumery employing known odiferous perfumery ingredients, e.g., techniques and ingredients mentioned in the standard textbooks "Soap, Perfumery and Cosmetics" by W. A. Poucher, 7th edition; published by Chapman & Hall (London), 1959; "Perfume and Flavour Chemicals" by S. Arctander, published by the author (Montclair) 1959 and "Perfume and Flavour Materials of Natural Origin" also by S. Arctander, self-published, Elizabeth N.J., 1960. Specific natural odoriferous ingredients which may be blended with the materials of disclosure include vetivert oil, guaiac wood oil, lemon oil, rose absolute, jasmin absolute, geranium oil, geraniol, lanvandin oil, acetate, patchouli oil, petitgrain oil, bergamot oil, clove bud oil, bay oil, nutmeg oil, pimento berry oil, ylang oil, sandalwood oil, clary sage oil, labdamun resin, orange oil, olibanum resin, mandarin oil, neroli oil, oakmoss, cedarwood oil and many others known to perfumers.

As used herein, the phrase "consumer product" refers to composition that is in a form ready for use by the consumer for the marketed indication. A solvent suitable for use in a consumer product is a solvent that, when combined with other components of the end product, will not render the consumer product unfit for its intended consumer use.

In accordance with this disclosure, isomeric alkoxynonenols, in particular, isomeric 8-alkoxy-4,8-dimethylnon-1-en-3-ols, provide attractive sandalwood odor that can blend harmoniously with other floral, woody and musky materials with a character lift perceived throughout the perfume composition. It has been found that isomeric alkoxynonenols, in particular, isomeric 8-alkoxy-4,8-dimethylnon-1-en-3-ols, can be blended with an extremely wide range of perfumery compositions, particularly those having a fresh floral, woody odor type with desirable odor effect.

Any one of the isomeric alkoxynonenol, in particular, isomeric 8-alkoxy-4,8-dimethylnon-1-en-3-ol, compositions of this disclosure can be included in a fragrance composition. In one embodiment, any one of the isomeric alkoxynonenol, in particular, isomeric 8-alkoxy-4,8-dimethylnon-1-en-3-ol, compositions of this disclosure is provided in a fragrance composition.

As described herein, this disclosure relates to a composition comprising at least one isomeric alkoxynonenol, in particular, isomeric 8-alkoxy-4,8-dimethylnon-1-en-3-ol, in an amount effective to impart a fragrance to the composition.

Also, as described herein, this disclosure relates to a fragrance comprising at least one isomeric alkoxynonenol, in particular, isomeric 8-alkoxy-4,8-dimethylnon-1-en-3-ol, in an amount effective to impart a fragrance to the composition.

Illustrative isomeric alkoxynonenols, in particular, isomeric 8-alkoxy-4,8-dimethylnon-1-en-3-ols, include, for example, isomers of 8-methoxy-4,8-dimethylnon-1-en-3-ol, 8-ethoxy-4,8-dimethylnon-1-en-3-ol, 8-propoxy-4,8-dimethylnon-1-en-3-ol, 8-isopropoxy-4,8-dimethylnon-1-en-3-ol, 8-butoxy-4,8-dimethylnon-1-en-3-ol, 8-isobutoxy-4,8-dimethylnon-1-en-3-ol, 8-pentyloxy-4,8-dimethylnon-1-en-3-ol, and 8-hexyloxy-4,8-dimethylnon-1-en-3-ol.

Preferred isomeric alkoxynonenols, in particular, isomeric 8-alkoxy-4,8-dimethylnon-1-en-3-ols, of this disclosure can be represented by the formula Formula I

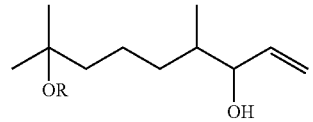

R = Me, Et, propyl, iso-propyl, butyl, iso-butyl, pentyl, hexyl

For the fragrance compositions of this disclosure, the at least one isomeric alkoxynonenols, in particular, isomeric 8-alkoxy-4,8-dimethylnon-1-en-3-ols, is present in an amount of at least about 1 ppm by weight, based on the total weight of the composition, to impart a fragrance to the composition.

For the fragrance compositions of this disclosure, the at least one isomeric alkoxynonenol, in particular, isomeric 8-alkoxy-4,8-dimethylnon-1-en-3-ol, can be combined with geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethyl-benzyl carbinol, trichloromethylphenyl carbinyl acetate, p-tert-butylcyclohexyl acetate, isononyl acetate, vetiveryl acetate, vetiverol, alpha-hexylcinnam-aldehyde, 2-methyl-3-(p-tert-butylphenyl)-propanal, 2-methyl-3-(p-isopropylphenyl)-propanal, 3-(p-tert-butylphenyl)-propanal, tricyclodecenyl acetate, tricyclodecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy-3-pentyl-tetrahydropyran, 3-carboxymethyl-2-pentyl-cyclopentane, 2-n-heptylcyclopentanone, 3-methyl-2-pentyl-2-cyclopentenone, n-decanal, n-dodecanal, 9-decen-1-ol, phenoxyethylisobutyrate, phenylacetaldehydedi-methylacetal, phenylacetaldehyde-diethylacetal, geranylnitrile, citronellylnitrile, cedrylacetate, 3-isocamphylcyclohexanol, cedrylmethyl ether, isolongifolanone, aubepinitrile, aubepine, heliotripine, coumarin, eugenol, vanillin, diphenyl oxide, hydroxycitronellal, ionones, methylionones, isomethylionones, irones, cis-3-hexenol and esters of the latter, indan-musks, tetraline-musks, isochromane-musks, macrocyclic ketones, macrolactone-musks, ethylene brassylate, or aromatic nitromusks, to impart a fragrance to the composition.

In an embodiment, this disclosure also relates in part to the preparation of isomeric alkoxynonenols, in particular, isomeric 8-alkoxy-4,8-dimethylnon-1-en-3-ols, for use in fragrance formulations. These isomeric alkoxynonenols, in particular, isomeric 8-alkoxy-4,8-dimethylnon-1-en-3-ols, have a range of unexpected and unobvious organoleptic properties described as provide attractive sandalwood odor that can blend harmoniously with other floral, woody and musky materials with a character lift perceived throughout the perfume composition. Further, the isomeric alkoxynonenols, in particular, isomeric 8-alkoxy-4,8-dimethylnon-1-en-3-ols, can be blended with an extremely wide range of perfumery compositions, particularly those having a fresh floral, woody odor type with desirable odor effect. These notes are highly desirable in creating consumer acceptable fragrances.

In accordance with this disclosure, the isomeric alkoxynonenols, in particular, isomeric 8-alkoxy-4,8-dimethylnon-1-en-3-ols, of this disclosure can be prepared by conventional processes. The compositions of this disclosure and the fragrance compositions of this disclosure can also be prepared by conventional processes.

As described herein, this disclosure provides a consumer product containing the fragrance composition comprising at least one isomeric alkoxynonenol, in particular, isomeric 8-alkoxy-4,8-dimethylnon-1-en-3-ol, in an amount effective to impart a fragrance to the consumer product.

As further described herein, this disclosure provides a method of imparting a fragrance to a consumer product comprising adding to the consumer product a fragrance composition comprising at least one isomeric alkoxynonenol, in particular, isomeric 8-alkoxy-4,8-dimethylnon-1-en-3-ol, in an amount effective to impart a fragrance to the consumer product.

Illustrative consumer fragrance products useful in this disclosure include, for example, a candle, an air care product, a perfume, a cologne, a soap, a personal care product, a detergent, a fabric care product, a household cleaning product, and the like.

More particularly, illustrative consumer fragrance products include a soap, a detergent, an air freshener, a room spray, a pomander, a candle, and a cosmetic comprising a cream, an ointment, a toilet water, a pre-shave lotion, an aftershave lotion, a talcum powder, a hair-care agent, a body deodorant, and an anti-perspirant.

Preferred illustrative consumer fragrance products include an air care product, a perfume, and a cologne.

In an embodiment, one or more of the isomeric alkoxynonenols, in particular, isomeric 8-alkoxy-4,8-dimethylnon-1-en-3-ols, of the present disclosure, alone or in combination with other co-ingredients, can be employed in fragrance compositions, solvents, media and the like. As indicated herein, the use of such isomeric alkoxynonenols, in particular, isomeric 8-alkoxy-4,8-dimethylnon-1-en-3-ols, is applicable to a wide variety of products in the fragrance industry such as, but not limited to: candles; air fresheners; perfumes; colognes; personal care products such as soaps, deodorants, shampoos, conditioners, shower gels and shaving lotions; cosmetics such as lotions and ointments; as well as detergents; fabric care products and household cleaner/cleaning agents.

As the isomeric alkoxynonenols, in particular, isomeric 8-alkoxy-4,8-dimethylnon-1-en-3-ols, of the present disclosure are useful ingredients for the perfuming of various products, the present disclosure also concerns all different forms of the isomeric alkoxynonenols, in particular, isomeric 8-alkoxy-4,8-dimethylnon-1-en-3-ols, that can be advantageously employed in perfumery. Such forms include a composition including isomeric alkoxynonenols, in particular, isomeric 8-alkoxy-4,8-dimethylnon-1-en-3-ols, and a solvent commonly used in perfumery compositions. Examples of such solvents used in perfumery are known in the art and include, but are not limited to: dipropyleneglycol, diethyl phthalate, isopropyl myristate, benzyl benzoate, 2-(2-ethoxy)-1-ethanol, ethyl citrate, ethanol, water/ethanol mixtures, limonene or other terpenes, isoparaffins such as those known under the trademark Isopar™ (ExxonMobil Chemicals, Houston, Tex.), and glycol ethers and glycol ether esters such as those known under the trademark Dowanol™ (Dow Chemical Company, Midland Mich.).

The isomeric alkoxynonenols, in particular, isomeric 8-alkoxy-4,8-dimethylnon-1-en-3-ols, of the present disclosure are particularly valuable as being capable of imparting milky and creamy sandalwood odor with shades of floral notes to perfume formulations. For fragrance applications, typical concentrations of the isomeric alkoxynonenols, in particular, isomeric 8-alkoxy-4,8-dimethylnon-1-en-3-ols, are on the order of 1 ppm to 1% by weight, or more, based on the total weight of the composition into which the fragrance compound is incorporated. Those skilled in the art will be able to employ the desired level of the compounds of the disclosure to provide the desired fragrance and intensity. In general, the isomeric alkoxynonenols, in particular, isomeric 8-alkoxy-4,8-dimethylnon-1-en-3-ols, of the present disclosure will be used in relatively small amounts, typically via significant dilutions due to their high-impact, diffusive properties.

The perfuming compositions according to the disclosure may be in the form of a simple mixture of the various co-ingredients and solvents, or also in the form of a biphasic system such as an emulsion or microemulsion. Such systems are well-known to persons skilled in the art.

As described herein, suitable perfumed end products that can include a composition of the present disclosure including, but are not limited to: 1) candles, air fresheners, perfumes and colognes, 2) personal care products such as soaps, deodorants, shampoos, conditioners, shower gels and shaving lotions; 3) cosmetics such as lotions and ointments; as well as 4) detergents, fabric care products and household cleansers/cleaning agents. Depending on the solvents that may be present in some end products, it may be necessary to protect the isomeric alkoxynonenols from premature degradation, for example by encapsulation or with a stabilizer, or other methods well-known to those of ordinary skill in the art.

The compositions of the present disclosure can also be added to, for example: 1) fragrance products; perfume; eau de perfume; eau de toilet; eau de cologne; and the like; skin-care cosmetics, face washing creams, varnishing creams, cleansing creams, cold creams, massage creams and oils, milky lotions, skin toning lotion, cosmetic solutions, packs, makeup remover, and the like; 2) makeup cosmetics, foundations, face powders, pressed powders, talcum powders, lip sticks, lip creams, cheek powders, eyeliners, mascara, eye shadows, eyebrow pencils, eye packs, nail enamels, nail enamel removers, and the like; 3) hair care cosmetics, pomades, brilliantines, setting lotions, hair sticks, hair solids, hair oils, hair treatments, hair creams, hair tonics, hair liquids, hair sprays, hair restorers, hair dyes, and the like; 4) sunburn cosmetics, suntan products, sunscreen products, and the like; 5) medical cosmetics, antiperspirants, after-shave lotions and gels, permanent wave lotions, medicated soaps, medicated shampoos, medicated skin care products, and the like; 6) hair care products, shampoos, rinses, shampoo-including-rinses, hair conditioners, hair treatments, hair packs, and the like; 7) as soaps, toilet soaps, bath soaps, perfumed soaps, transparent soaps, synthetic soaps, and the like; 8) body washing soaps, body soaps, body shampoos, hand soaps, and the like; 9) bathing, bathing agents (e.g., bath salts, bath tablets, bath liquids, and the like), foam baths (bubble bath and the like), bath oils (e.g., bath perfumes, bath capsules and the like), milk baths, bath gels, bath cubes, and the like; 10) detergents, heavy duty detergents for clothes, light duty detergents for clothes, liquid detergents, laundering soaps, compact detergents, powder soaps, and the like; 11) softening finishing agents, softeners, furniture care products, and the like; and deodorants, aromatic substances and the like; and 12) insect repellent, insecticides, and the like.

Fragrances in consumer products provide several functions. They mask base odors, provide aesthetic pleasure and signal product attributes and function to the user, e.g., hygiene, cleanliness, mildness. Notwithstanding these benefits, it is also true that perfumes can cause a myriad of problems within products they have been added to, e.g., discoloration, phase separation, problems such as irritation and occasional allergic reaction to the user. Additionally, fragrances represent one of the more expensive components of the product and many fragrance ingredients may not be easily biodegradable. Over the years, perfume levels in many consumer products have increased by the popular demand but at the same time consumers have also become more critical of the fragranced products they purchase and use.

The quantities in which the compositions of this disclosure can be used in perfume compositions or in products to be perfumed can vary within wide limits and depend inter alia on the nature of the product in which the fragrance material is used, on the nature and quantity of the other components in the perfume composition and on the odor effect which is aimed at. It is therefore only possible to specify very rough limits, which, however, provide sufficient information for the specialist to be able to use the compounds according to the disclosure independently. In most cases a quantity of only 1 ppm in a perfume composition will already be sufficient to obtain a clearly perceptible odor effect. On the other hand, to achieve special odoriferous effects it is possible to use quantities of 100, 1000, 5000 ppm or even more in a composition. In products perfumed with such compositions, these concentrations are proportionately lower, depending on the quantity of composition used in the product.

There are three basic stages of a fragrance. The first stage (i.e., top notes) is the first impression that a fragrance gives to a customer. This initial stage is the most volatile. In the second stage (i.e., middle notes), a few moments after the application of a fragrance, the heart is revealed. This modifying part of the fragrance has medium volatility. In the third stage (i.e., base notes), after a fragrance dries down, these notes are more pronounced. This part of the fragrance is the longest lasting. The balance between these three groups is very important. In a well-balanced fragrance, it is important to understand what group or groups are the most important for a particular application. The fragrance compositions of this disclosure exemplify a desirable balance between these three groups for desired applications.

While we have shown and described several embodiments in accordance with our disclosure, it is to be clearly understood that the same may be susceptible to numerous changes apparent to one skilled in the art. Therefore, we do not wish to be limited to the details shown and described but intend to show all changes and modifications that come within the scope of the appended claims.

The following examples are only to illustrate the preparation and use of the compounds according to the disclosure. The disclosure is not limited thereto.

EXAMPLE 1

Preparation of
8-Methoxy-4,8-dimethylnon-1-en-3-ol

A solution of 4.73 moles of commercially available 6-methoxy-2,6-dimethylheptanal in 815 grams of THF was gradually added with stirring to a solution of 4.7 moles of vinyl magnesium chloride in THF (2M) at a temperature of 20° C. to 25° C. The crude product thus obtained was poured gradually into 3.5 L of an aqueous citric acid solution containing 10% acid by weight. The temperature during this quench is <25 C. The oil layer was removed and the aqueous phase was extracted with 300 ml of cyclohexane twice. The combined organic phases were washed with 500 ml of 10% sodium carbonate solution. The organic phase was further washed with water until the pH of the water layer was below 10.

The crude reaction mixture was stripped of solvent and distilled through a short path distillation unit. The collected product boiling point was 55° C. at 0.5 mmHg vacuum. The reaction yielded 902 grams of 98.2% pure product. The product can be further purified to >99% by redistilling it through a 16" Goodloe distillation unit.

EXAMPLE 2

Preparation of 8-Ethoxy-4,8-dimethylnon-1-en-3-ol 1 mole equivalent of 6-ethoxy-2,6-dimethylheptanal, prepared according to the method of preparation disclosed in the U.S. Pat. No. 7,842,842 B1, dissolved in 250 ml of THF was added with stirring to a solution of 1 mole equivalent of vinyl magnesium chloride in THF (2M) at a temperature of 20° C. to 25° C. The product thus obtained was poured gradually into 1 litre of an aqueous 10% citric acid solution while maintaining 25° C. temperature. The organic layer was removed and the aqueous layer extracted with cyclohexane. The combined organic phases were washed with sodium carbonate solution until the pH of the water layer was below 10.

The crude product was stripped of solvent and distilled a short path distillation unit under reduced pressure. The product was further distilled to a high purity grade by redistilling it using a Goodloe column to yield approximately 190 grams of 8-ethoxy-4,8-dimethylnon-1-en-3-ol.

EXAMPLE 3

Preparation of Fragrance Formulation Containing 8-Methoxy-4,8-dimethylnon-1-en-3-ol A perfume composition was formulated using 8-methoxy-4,8-dimethylnon-1-en-3-ol in an appropriate quantity to provide fresh, floral, woody, ambery odor emphasizing sandalwood notes.

| | |
|---|---|
| Ambrettolide | 2.50 |
| Cetalox | 4.00 |
| Calone 1951 | 5.50 |
| Cedramber | 2.00 |
| Dihydroeugenol | 0.50 |
| DPG | 852.50 |
| Elemi oil | 4.00 |
| Helional | 25.00 |
| Iso-e-super | 31.00 |
| Iso-bornyl acetate | 2.00 |
| Javanol (10% IPM) | 2.00 |
| Methylthiazolyl ethanol 4,5-/Sulfurol 1% TEC | 1.00 |
| Nerolidol | 2.00 |
| Terpineol | 2.00 |
| Cyclamen aldehyde | 5.00 |
| Bergamot | 20.00 |
| Polvolide | 5.00 |
| Sandalore | 12.00 |
| Melonal | 7.00 |
| Grapefruit Base | 3.00 |
| Orange oil | 7.00 |
| Timberol 10% BB | 2.50 |
| 8-methoxy-4,8-dimethylnon-1-en-3-ol | 2.50 |
| Total | 1000.00 |

The present disclosure is not to be limited in scope by the specific embodiments described herein. Indeed, various modifications of the disclosure in addition to those described herein will become apparent to those skilled in the art from the foregoing description. Such modifications are intended to fall within the scope of the appended claims.

What is claimed is:

1. A composition comprising at least one isomeric 8-alkoxy-4,8-dimethylnon-1-en-3-ol in an amount effective to impart a fragrance to the composition.

2. The composition of claim 1 wherein the at least one isomeric 8-alkoxy-4,8-dimethylnon-1-en-3-ol is selected from the group consisting of 8-methoxy-4,8-dimethylnon-1-en-3-ol, 8-ethoxy-4,8-dimethylnon-1-en-3-ol, 8-propoxy-4,8-dimethylnon-1-en-3-ol, 8-isopropoxy-4,8-dimethylnon-1-en-3-ol, 8-butoxy-4,8-dimethylnon-1-en-3-ol, 8-isobutoxy-4,8-dimethylnon-1-en-3-ol, 8-pentyloxy-4,8-dimethylnon-1-en-3-ol, and 8-hexyloxy-4,8-dimethylnon-1-en-3-ol.

3. The composition of claim 1 wherein the at least one isomeric 8-alkoxy-4,8-dimethylnon-1-en-3-ol is represented by the formula

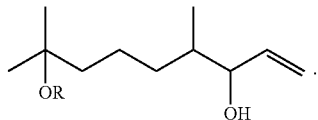

Formula I

R = Me, Et, propyl, iso-propyl, butyl, iso-butyl, pentyl, hexyl

4. The composition of claim 1 wherein the at least one isomeric 8-alkoxy-4,8-dimethylnon-1-en-3-ol is present in an amount of at least about 1 ppm by weight, based on the total weight of the composition, to impart a fragrance to the composition.

5. The composition of claim 1 wherein the at least one isomeric 8-alkoxy-4,8-dimethylnon-1-en-3-ol is combined with geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethyl-benzyl carbinol, trichloromethylphenyl carbinyl acetate, p-tert-butylcyclohexyl acetate, isononyl acetate, vetiveryl acetate, vetiverol, alpha-hexyl-cinnam-aldehyde, 2-methyl-3-(p-tert-butylphenyl)-propanal, 2-methyl-3-(p-isopropylphenyl)-propanal, 3-(p-tert-butylphenyl)-propanal, tricyclodecenyl acetate, tricyclodecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy-3-pentyl-tetrahydropyran, 3-carboxymethyl-2-pentylcyclopentane, 2-n-heptylcyclopentanone, 3-methyl-2-pentyl-2-cyclopentenone, n-decanal, n-dodecanal, 9-decen-1-01, phenoxyethylisobutyrate, phenylacetaldehydedi-methylacetal, phenylacetaldehyde-diethylacetal, geranylnitrile, citronellylnitrile, cedrylacetate, 3-isocamphylcyclohexanol, cedrylmethyl ether, isolongifolanone, aubepinitrile, aubepine, heliotripine, coumarin, eugenol, vanillin, diphenyl oxide, hydroxycitronellal, ionones, methylionones, isomethylionones, irones, cis-3-hexenol and esters of the latter, indan-musks, tetraline-musks, isochromane-musks, macrocyclic ketones, macrolactone-musks, ethylene brassylate, or aromatic nitromusks, to impart a fragrance to the composition.

6. A fragrance composition comprising at least one isomeric 8-alkoxy-4,8-dimethylnon-1-en-3-ol in an amount effective to impart a fragrance to the composition.

7. The fragrance composition of claim 6 wherein the at least one isomeric 8-alkoxy-4,8-dimethylnon-1-en-3-ol is selected from the group consisting of 8-methoxy-4,8-dimethylnon-1-en-3-ol, 8-ethoxy-4,8-dimethylnon-1-en-3-ol, 8-propoxy-4,8-dimethylnon-1-en-3-ol, 8-isopropoxy-4,8-dimethylnon-1-en-3-ol, 8-butoxy-4,8-dimethylnon-1-en-3-ol, 8-isobutoxy-4,8-dimethylnon-1-en-3-ol, 8-pentyloxy-4,8-dimethylnon-1-en-3-ol, and 8-hexyloxy-4,8-dimethylnon-1-en-3-ol.

8. The fragrance composition of claim 6 wherein the at least one isomeric 8-alkoxy-4,8-dimethylnon-1-en-3-ol is represented by the formula

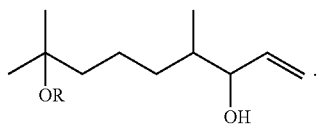

Formula I

R = Me, Et, propyl, iso-propyl, butyl, iso-butyl, pentyl, hexyl

9. The fragrance composition of claim 6 wherein the at least one isomeric 8-alkoxy-4,8-dimethylnon-1-en-3-ol is present in an amount of at least about 1 ppm by weight, based on the total weight of the composition, to impart a fragrance to the composition.

10. The fragrance composition of claim 6 wherein the at least one isomeric 8-alkoxy-4,8-dimethylnon-1-en-3-ol is combined with geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethyl-benzyl carbinol, trichloromethylphenyl carbinyl acetate, p-tert-butylcyclohexyl acetate, isononyl acetate, vetiveryl acetate, vetiverol, alpha-hexylcinnam-aldehyde, 2-methyl-3-(p-tert-butylphenyl)-propanal, 2-methyl-3-(p-isopropylphenyl)-propanal, 3-(p-tert-butylphenyl)-propanal, tricyclodecenyl acetate, tricyclodecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy-3-pentyl-tetrahydropyran, 3-carboxymethyl-2-pentylcyclopentane, 2-n-heptylcyclopentanone, 3-methyl-2-pentyl-2-cyclopentenone, n-decanal, n-dodecanal, 9-decen-1-ol, phenoxyethylisobutyrate, phenylacetaldehydedi-methylacetal, phenylacetaldehyde-diethylacetal, geranylnitrile, citronellylnitrile, cedrylacetate, 3-isocamphylcyclohexanol, cedrylmethyl ether, isolongifolanone, aubepinitrile, aubepine, heliotripine, coumarin, eugenol, vanillin, diphenyl oxide, hydroxycitronellal, ionones, methylionones, isomethylionones, irones, cis-3-hexenol and esters of the latter, indan-musks, tetraline-musks, isochromane-musks, macrocyclic ketones, macrolactone-musks, ethylene brassylate, or aromatic nitromusks, to impart a fragrance to the composition.

11. A perfume composition comprising at least one isomeric 8-alkoxy-4,8-dimethylnon-1-en-3-ol in an amount effective to impart a fragrance to the composition.

12. The perfume composition of claim 11 wherein the at least one isomeric 8-alkoxy-4,8-dimethylnon-1-en-3-ol is selected from the group consisting of 8-methoxy-4,8-dimethylnon-1-en-3-ol, 8-ethoxy-4,8-dimethylnon-1-en-3-ol, 8-propoxy-4,8-dimethylnon-1-en-3-ol, 8-isopropoxy-4,8-dimethylnon-1-en-3-ol, 8-butoxy-4,8-dimethylnon-1-en-3-ol, 8-isobutoxy-4,8-dimethylnon-1-en-3-ol, 8-pentyloxy-4,8-dimethylnon-1-en-3-ol, and 8-hexyloxy-4,8-dimethylnon-1-en-3-ol.

13. The perfume composition of claim 11 wherein the at least one isomeric 8-alkoxy-4,8-dimethylnon-1-en-3-ol is represented by the formula

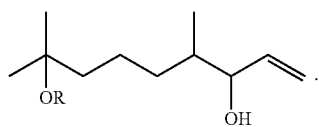

Formula I

R = Me, Et, propyl, iso-propyl, butyl, iso-butyl, pentyl, hexyl

14. The perfume composition of claim 11 wherein the at least one isomeric 8-alkoxy-4,8-dimethylnon-1-en-3-ol is present in an amount of at least about 1 ppm by weight, based on the total weight of the composition, to impart a fragrance to the composition.

15. The perfume composition of claim 11 wherein the at least one isomeric 8-alkoxy-4,8-dimethylnon-1-en-3-ol is combined with geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethyl-benzyl carbinol, trichloromethylphenyl carbinyl acetate, p-tert-butylcyclohexyl acetate, isononyl acetate, vetiveryl acetate, vetiverol, alpha-hexylcinnam-aldehyde, 2-methyl-3-(p-tert-butylphenyl)-propanal, 2-methyl-3-(p-isopropylphenyl)-propanal, 3-(p-tert-butylphenyl)-propanal, tricyclodecenyl acetate, tricyclodecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy-3-pentyl-tetrahydropyran, 3-carboxymethyl-2-pentylcyclopentane, 2-n-heptylcyclopentanone, 3-methyl-2-pentyl-2-cyclopentenone, n-decanal, n-dodecanal, 9-decen-1-ol, phenoxyethylisobutyrate, phenylacetaldehydedi-methylacetal, phenylacetaldehyde-diethylacetal, geranylnitrile, citronellylnitrile, cedrylacetate, 3-isocamphylcyclohexanol, cedrylmethyl ether, isolongifolanone, aubepinitrile, aubepine, heliotripine, coumarin, eugenol, vanillin, diphenyl oxide, hydroxycitronellal, ionones, methylionones, isomethylionones, irones, cis-3-hexenol and esters of the latter, indan-musks, tetraline-musks, isochromane-musks, macrocyclic ketones, macrolactone-musks, ethylene brassylate, or aromatic nitromusks, to impart a fragrance to the composition.

16. A consumer product containing the perfume composition of claim 11.

17. The consumer product of claim 16 selected from the group consisting of a candle, an air care product, a perfume, a cologne, a soap, a personal care product, a detergent, a fabric care product, and a household cleaning product.

18. The consumer product of claim 16 selected from the group consisting of a soap, a detergent, an air freshener, a room spray, a pomander, a candle, and a cosmetic comprising a cream, an ointment, a toilet water, a pre-shave lotion, an aftershave lotion, a talcum powder, a hair-care agent, a body deodorant, and an anti-perspirant.

19. The consumer product of claim 18 selected from the group consisting of an air care product, a perfume, and a cologne.

20. A method of imparting a fragrance to a consumer product comprising adding to the consumer product a fragrance composition comprising at least one isomeric 8-alkoxy-4,8-dimethylnon-1-en-3-ol in an amount effective to impart a fragrance to the consumer product.

* * * * *